United States Patent
Shibasaki et al.

(10) Patent No.: US 9,951,067 B2
(45) Date of Patent: Apr. 24, 2018

(54) OPTICALLY ACTIVE α-TRIFLUOROMETHYL-β-AMINO ACID DERIVATIVE PRODUCTION METHOD

(71) Applicant: Microbial Chemistry Research Foundation, Tokyo (JP)

(72) Inventors: Masakatsu Shibasaki, Tokyo (JP); Naoya Kumagai, Tokyo (JP); Liang Yin, Tokyo (JP)

(73) Assignee: Microbial Chemistry Research Foundation (JP)

( * ) Notice: Subject to any disclaimer, the term of this patent is extended or adjusted under 35 U.S.C. 154(b) by 0 days.

(21) Appl. No.: 15/513,635

(22) PCT Filed: Sep. 18, 2015

(86) PCT No.: PCT/JP2015/076816
§ 371 (c)(1),
(2) Date: Mar. 23, 2017

(87) PCT Pub. No.: WO2016/047644
PCT Pub. Date: Mar. 31, 2016

(65) Prior Publication Data
US 2017/0283411 A1    Oct. 5, 2017

(30) Foreign Application Priority Data
Sep. 24, 2014   (JP) .................................. 2014-193476

(51) Int. Cl.
| | |
|---|---|
| C07D 401/02 | (2006.01) |
| C07D 401/10 | (2006.01) |
| C07D 401/14 | (2006.01) |
| C07D 471/04 | (2006.01) |
| B01J 31/24 | (2006.01) |

(52) U.S. Cl.
CPC ........ *C07D 471/04* (2013.01); *B01J 31/2409* (2013.01); *B01J 2231/50* (2013.01); *B01J 2531/16* (2013.01); *C07B 2200/07* (2013.01)

(58) Field of Classification Search
CPC ... C07D 401/02; C07D 401/10; C07D 401/14
USPC .......................... 546/119, 121; 514/300, 303
See application file for complete search history.

(56) References Cited

U.S. PATENT DOCUMENTS 6,478,250 B1   11/2002   Kobayashi et al.

FOREIGN PATENT DOCUMENTS

JP       2003-260366       9/2003

OTHER PUBLICATIONS

Brewitz et al., Journal of the American Chemical Society (2015), 137(50), 15929-15939.*
Salwiczek, M. et al., "Fluorinated amino acids: compatibility with native protein structures and effects on protein-protein interactions," Chem. Soc. Rev., vol. 41, pp. 2135-2171 (2012).
Itoh, Y. et al., "Dipole Interaction-Controlled Stereoselectivity in Aldol Reaction of alpha-CF3 Enolate with Fluoral," Organic Letters, vol. 5, No. 25, pp. 4807-4809 (2003).
Itoh, Y. et al., "Direct Generation of Ti-Enolate of alpha-CF3 Ketone: Theoretical Study and High-Yielding and Diastereoselective Aldol Reaction," J. Am. Chem. Soc., vol. 126, pp. 13174-13176 (2004).
Shimada, T. et al. "Highly Stereoselective TiCl4-Catalyzed Evans-Aldol and Et3Al-Mediated Reformatsky Reactions. Efficient Accesses to Optically Active syn- or anti-alpha-Trifluoroemethyl-beta-hydroxy Carboxylic Acid Derivatives," Organic Letters, vol. 8, No. 6, pp. 1129-1131 (2006).
Mikami, K. et al., "Metal Enolates of alpha-CF3 Ketones: Theoretical Guideline, Direct Generation, and Synthetic Use," The Chemical Record, vol. 6, pp. 1-11 (2006).
Yin, L. et al., "Catalytic Generation of alpha-CF3 Enolate: Direct Catalytic Asymmetric Mannich-Type Reaction of alpha-CF3 Amide," J. Am. Chem. Soc., vol. 136, pp. 17958-17961 (2014).
Shimada, T. et al., "First highly stereoselective synthesis of anti-alpha-trifluoromethyl-beta-amino acid derivatives," Chem. Comm., pp. 3628-3630 (2006).
Orin, Y. et al., "Asymmetric Mannich-Type Reaction Using Alkenyl Trichloroacetates Catalyzed by a Chiral Phosphine-Silver Complex," The 92nd CSJ Annual Meeting (2012) lecture proceedings IV (Mar. 9, 2012), p. 1697.

* cited by examiner

*Primary Examiner* — Niloofar Rahmani
(74) *Attorney, Agent, or Firm* — Carmody Torrance Sandak & Hennessey LLP

(57) ABSTRACT

A method for producing an optically active α-trifluoromethyl-β-amino acid derivative, the method including: allowing a compound represented by the following General Formula (1) and a compound represented by the following General Formula (2) to react in the presence of a copper-optically active phosphine complex obtained from a copper compound and an optically active phosphine compound, to thereby obtain an optically active α-trifluoromethyl-β-amino acid derivative represented by the following General Formula (3):

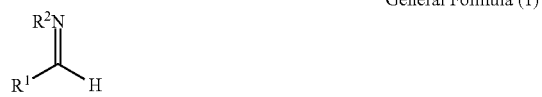

General Formula (1)

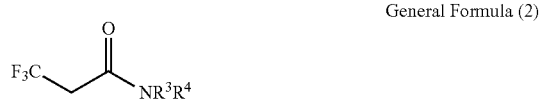

General Formula (2)

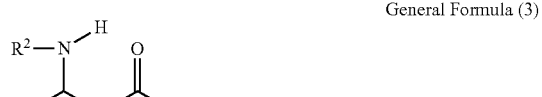

General Formula (3)

7 Claims, No Drawings

OPTICALLY ACTIVE α-TRIFLUOROMETHYL-β-AMINO ACID DERIVATIVE PRODUCTION METHOD

TECHNICAL FIELD

The present invention relates to a method for producing an optically active α-trifluoromethyl-β-amino acid derivative.

BACKGROUND ART

Optically active β-amino acids and derivatives thereof are useful chiral building blocks in organic synthetic chemistry, especially medicinal synthetic chemistry.

One useful synthesis method for the optically active β-amino acids and derivatives thereof is asymmetric Mannich reaction. One example of the asymmetric Mannich reaction is presented in the following Scheme 1.

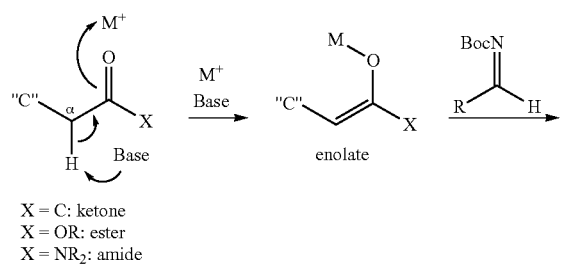

X = C: ketone
X = OR: ester
X = NR$_2$: amide

In the asymmetric Mannich reaction, as presented in the above Scheme 1, use of a base and a metal (M$^+$) deprotonates a carbonyl compound where a hydrogen atom is bonded to carbon at the α-position relative to the carbonyl carbon, to thereby form an enolate which is an active intermediate. Furthermore, by reacting the enolate with an imine which is an electrophile, a carbon-carbon bond is formed to obtain an optically active β-amino acid derivative having two asymmetric points. Here, when the base and the metal are used in amounts equal to or more than the amount of a starting material, the reaction becomes an equivalent reaction. When they are used in catalytic amounts, the reaction becomes a catalytic reaction.

20% or more of the currently sold pharmaceutical products contain at least one fluorine atom (see, for example, NPL 1). Therefore, a fluorine atom is desirably contained also in the optically active β-amino acids and derivatives thereof, which are synthesis intermediates of pharmaceutical products and useful chiral building blocks.

In the asymmetric Mannich reaction, when "C" is a usual alkyl group, the reaction of the Scheme 1 proceeds. When "C" is a CF$_3$ group, however, β-elimination, which is a side reaction, preferentially proceeds as presented in the following Scheme 2. This raises a problem that the yield rate of a desired optically active β-amino acid derivative considerably decreases.

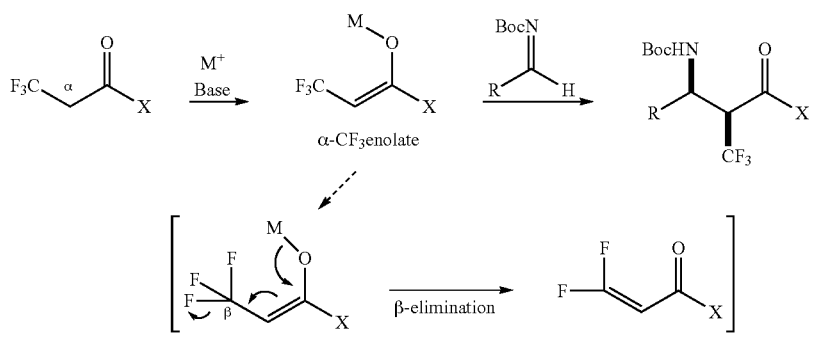

Various studies have been made on the Mannich reaction using a carbonyl compound where a CF$_3$ group is bonded to carbon at the α-position relative to the carbonyl carbon (see, for example, NPLs 2 to 5). In these studies, however, there are problems such as being a racemic synthesis, use of reagents more than equivalent amounts, and consumption of a large amount of optically active compounds by using chiral auxiliary groups.

Therefore, at present, there is a demand for providing a method for producing an optically active α-trifluoromethyl-β-amino acid derivative, the method being able to synthesize the optically active α-trifluoromethyl-β-amino acid derivative at high yield and catalytically without necessitating activating reagents more than equivalent amounts.

CITATION LIST

Non-Patent Literature

NPL 1: Salwiczek M. et al., Chem. Soc. Rev., 2012, 41, 2135-2171.
NPL 2: Mikami K. et. al., Org. Lett., 2003, Vol. 5, No. 25, 4807-4809.
NPL 3: Mikami K. et. al., J. Am. Chem. Soc., 2004, 126, 13174-13175.
NPL 4: Ishihara T. et. al., 2006, Vol. 8, No. 6, 1129-1131.
NPL 5: Mikami K. et. al., Chem. Record, 2006, 6, 1-11.

SUMMARY OF INVENTION

Technical Problem

The present invention aims to solve the above existing problems and achieve the following object. That is, an object of the present invention is to provide a method for producing an optically active α-trifluoromethyl-β-amino acid derivative, the method being able to synthesize the optically active α-trifluoromethyl-1-amino acid derivative at high yield and catalytically without necessitating activating reagents more than equivalent amounts.

Solution to Problem

Means for solving the above problem are as follows.

A method of the present invention for producing an optically active α-trifluoromethyl-β-amino acid derivative includes allowing a compound represented by the following General Formula (1) and a compound represented by the following General Formula (2) to react in the presence of a copper-optically active phosphine complex obtained from a copper compound and an optically active phosphine compound, to thereby obtain an optically active α-trifluoromethyl-β-amino acid derivative represented by the following General Formula (3):

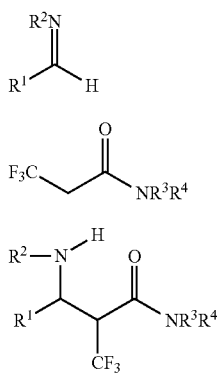

General Formula (1)

General Formula (2)

General Formula (3)

where in the General Formulas (1) to (3), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, $R^3$ and $R^4$ each independently represent a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and $R^3$ and $R^4$ may form a ring structure with N.

Advantageous Effects of Invention

The present invention can solve the above existing problems and achieve the above object, and can provide a method for producing an optically active α-trifluoromethyl-β-amino acid derivative, the method being able to synthesize the optically active α-trifluoromethyl-β-amino acid derivative at high yield and catalytically without necessitating activating reagents more than equivalent amounts.

DESCRIPTION OF EMBODIMENTS

Steric configurations in the chemical formulas and the general formulas described in the present specification and claims are absolute configurations unless otherwise specified.

(Method for Producing Optically Active α-Trifluoromethyl-β-Amino Acid Derivative)

A method of the present invention for producing an optically active α-trifluoromethyl-β-amino acid derivative is a method for producing an optically active α-trifluoromethyl-β-amino acid derivative including allowing a compound represented by the following General Formula (1) and a compound represented by the following General Formula (2) to react, to thereby obtain an optically active α-trifluoromethyl-β-amino acid derivative represented by the following General Formula (3).

The reaction is performed in the presence of a copper-optically active phosphine complex.

<Compound Represented by General Formula (1)>

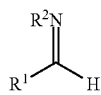

General Formula (1)

In the General Formula (1), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and $R^2$ represents a protective group of N.

<Compound Represented by General Formula (2)>

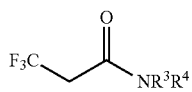

General Formula (2)

In the General Formula (2), $R^3$ and $R^4$ each independently represent a substituted or unsubstituted aryl group, a substituted or unsubstituted heteroaryl group, a substituted or unsubstituted alkyl group, a substituted or unsubstituted alkenyl group, or a substituted or unsubstituted alkynyl group. $R^3$ and $R^4$ may form a ring structure with N.

<Optically Active α-Trifluoromethyl-β-Amino Acid Derivative Represented by General Formula (3)>

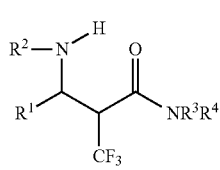

General Formula (3)

In the General Formula (3), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, and $R^3$ and $R^4$ each independently represent a substituted or unsubstituted aryl group, a substituted or unsubstituted heteroaryl group, a substituted or unsubstituted alkyl group, a substituted or unsubstituted alkenyl group, or a substituted or unsubstituted alkynyl group. $R^3$ and $R^4$ may form a ring structure with N.

The method of the present invention for producing an optically active α-trifluoromethyl-β-amino acid derivative utilizes so-called catalytic asymmetric Mannich reaction. This method binds carbon of an imino group in the compound represented by the General Formula (1) to carbon at the α-position relative to carbon of a carbonyl group in the compound represented by the General Formula (2).

In the General Formula (1) and the General Formula (3), the $R^1$ is preferably a substituted or unsubstituted aryl group because the yield will be excellent.

From the viewpoints of reactivity and stereoselectivity, the compound represented by the General Formula (2) is preferably a compound represented by the following General Formula (2-1), and the optically active α-trifluoromethyl-β-amino acid derivative represented by the General Formula (3) is preferably an optically active α-trifluoromethyl-β-amino acid derivative represented by the following General Formula (3-1).

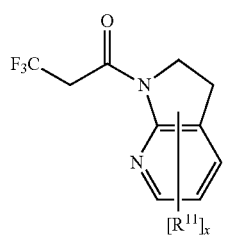

General Formula (2-1)

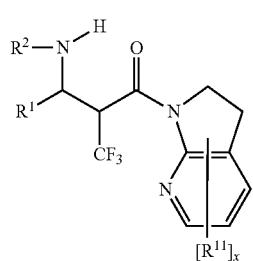

General Formula (3-1)

In the General Formula (2-1) and the General Formula (3-1), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, $R^{11}$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and x is an integer of 0 to 7 (where when x is 2 or more, $R^{11}$ may be identical or different).

Examples of the optically active α-trifluoromethyl-β-amino acid derivative represented by the General Formula (3) include an optically active β-trifluoromethyl-β-amino acid derivative represented by the following General Formula (3-A).

Examples of the optically active α-trifluoromethyl-β-amino acid derivative represented by the General Formula (3-1) include an optically active α-trifluoromethyl-β-amino acid derivative represented by the following General Formula (3-1-A).

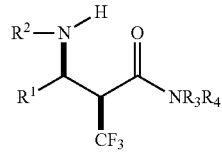

General Formula (3-A)

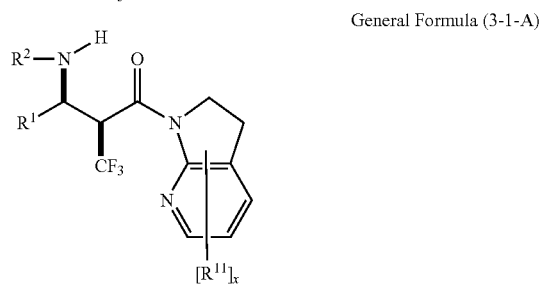

General Formula (3-1-A)

In the General Formula (3-A), $R^1$, $R^2$, $R^3$, and $R^4$ are the same as $R^1$, $R^2$, $R^3$, and $R^4$ in the General Formula (3).

In the General Formula (3-1-A), $R^1$, $R^2$, $R^1$, and x are the same as $R^1$, $R^2$, $R^{11}$, and x in the General Formula (3-1).

<<$R^2$>>

The $R^2$ is not particularly limited and may be appropriately selected depending on the intended purpose, so long as it is a protective group of N. Examples of the $R^2$ include a methoxycarbonyl group, a tert-butoxycarbonyl group, a benzyloxycarbonyl group, an allyloxycarbonyl group, a formyl group, an acetyl group, a benzoyl group, a methyl group, an ethyl group, an allyl group, and a benzenesulfonyl group. Among them, a tert-butoxycarbonyl group is preferable from the viewpoints of reactivity and stereoselectivity.

<<$R^1$, $R^3$, $R^4$, and $R^{11}$>>

Specific examples of the $R^1$, $R^3$, $R^4$, and $R^1$ will be described below.

—Aryl Group—

The aryl group is, for example, a monocyclic or condensed polycyclic aromatic hydrocarbon group. Examples of the aryl group include a phenyl group, a 1-naphthyl group, a 2-naphthyl group, an anthranyl group, and a phenanthryl group.

—Heteroaryl Group—

The heteroaryl group is, for example, a monocyclic heteroaryl, group or a condensed polycyclic heteroaryl group. The number of ring-constituting hetero atoms in the heteroaryl group is not particularly limited, but is one to several, preferably about 1 to about 5. When the heteroaryl group contains 2 or more ring-constituting hetero atoms, these may be identical or different. Examples of the hetero atoms include an oxygen atom, a nitrogen atom, and a sulfur atom.

——Monocyclic Heteroaryl Group——

Examples of the monocyclic heteroaryl group include 5-membered to 7-membered monocyclic heteroaryl groups. Examples such monocyclic heteroaryl groups include a 2-furyl group, a 3-furyl group, a 2-thienyl group, a 3-thienyl group, a 1-pyrrolyl group, a 2-pyrrolyl group, a 3-pyrrolyl group, a 2-oxazolyl group, a 4-oxazolyl group, a 5-oxazolyl group, a 3-isoxazolyl group, a 4-isoxazolyl group, a 5-isoxazolyl group, a 2-thiazolyl group, a 4-thiazolyl group, a 5-thiazolyl group, a 3-isothiazolyl group, a 4-isothiazolyl group, a 5-isothiazolyl group, a 1-imidazolyl group, a 2-imidazolyl group, a 4-imidazolyl group, a 5-imidazolyl group, a 1-pyrazolyl group, a 3-pyrazolyl group, a 4-pyrazolyl group, a 5-pyrazolyl group, a (1,2,3-oxadiazol)-4-yl group, a (1,2,3-oxadiazol)-5-yl group, a (1,2,4-oxadiazol)-3-yl group, a (1,2,4-oxadiazol)-5-yl group, a (1,2,5-oxadiazol)-3-yl group, a (1,2,5-oxadiazol)-4-yl group, a (1,3,4-oxadiazol)-2-yl group, a (1,3,4-oxadiazol)-5-yl group, a furazanyl group, a (1,2,3-thiadiazol)-4-yl group, a (1,2,3-thiadiazol)-5-yl group, a (1,2,4-thiadiazol)-3-yl group, a (1,2,4-thiadiazol)-5-yl group, a (1,2,5-thiadiazol)-3-yl group, a (1,2,5-thiadiazol)-4-yl group, a (1,3,4-thiadiazolyl)-2-yl group, a (1,3,4-thiadiazolyl)-5-yl group, a (1H-1,2,3-triazol)-1-yl group, a (1H-1,2,3-triazol)-4-yl group, a (1H-1,2,3-triazol)-5-yl group, a (2H-1,2,3-triazol)-2-yl group, a (2H-1,2,3-triazol)-4-yl group, a (1H-1,2,4-triazol)-1-yl group, a (1H-1,2,4-triazol)-3-yl group, a (1H-1,2,4-triazol)-5-yl group, a (4H-1,2,4-triazol)-3-yl group, a (4H-1,2,4-triazol)-4-yl group, a (1H-tetrazol)-1-yl group, a (1H-tetrazol)-5-yl group, a (2H-tetrazol)-2-yl group, a (2H-tetrazol)-5-yl group, a 2-pyridyl group, a 3-pyridyl group, a 4-pyridyl group, a 3-pyridazinyl group, a 4-pyridazinyl group, a 2-pyrimidinyl group, a 4-pyrimidinyl group, a 5-pyrimidinyl group, a 2-pyrazinyl group, a (1,2,3-triazin)-4-yl group, a (1,2,3-triazin)-5-yl group, a (1,2,4-triazin)-3-yl group, a (1,2,4-triazin)-5-yl group, a (1,2,4-triazin)-6-yl group, a (1,3,5-triazin)-2-yl group, a 1-azepinyl group, a 1-azepinyl group, a 2-azepinyl group, a 3-azepinyl group, a 4-azepinyl group, a (1,4-oxazepin)-2-yl group, a (1,4-oxazepin)-3-yl group, a (1,4-oxazepin)-5-yl group, a (1,4-oxazepin)-6-yl group, a (1,4-oxazepin)-7-yl group, a (1,4-thiazepin)-2-yl group, a (1,4-thiazepin)-3-yl group, a (1,4-thiazepin)-5-yl group, a (1,4-thiazepin)-6-yl group, and a (1,4-thiazepin)-7-yl group.

——Condensed Polycyclic Heteroaryl Group——

Examples of the condensed polycyclic heteroaryl group include 8-membered to 14-membered condensed polycyclic heteroaryl groups. Examples of such condensed polycyclic heteroaryl groups include a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzo[b]thienyl group, a 3-benzo[b]thienyl group, a 4-benzo[b]thienyl group, a 5-benzo[b]thienyl group, a 6-benzo[b]thienyl group, a 7-benzo[b]thienyl group, a 1-benzo[c]thienyl group, a 4-benzo[c]thienyl group, a 5-benzo[c]thienyl group, a 1-indolyl group, a 1-indolyl group, a 2-indolyl group, a 3-indolyl group, a 4-indolyl group, a 5-indolyl group, a 6-indolyl group, a 7-indolyl group, a (2H-isoindol)-1-yl group, a (2H-isoindol)-2-yl group, a (2H-isoindol)-4-yl group, a (2H-isoindol)-5-yl group, a (1H-indazol)-1-yl group, a (1H-indazol)-3-yl group, a (1H-indazol)-4-yl group, a (1H-indazol)-5-yl group, a (1H-indazol)-6-yl group, a (1H-indazol)-7-yl group, a (2H-indazol)-1-yl group, a (2H-indazol)-2-yl group, a (2H-indazol)-4-yl group, a (2H-indazol)-5-yl group, a 2-benzoxazolyl group, a 2-benzoxazolyl group, a 4-benzoxazolyl group, a 5-benzoxazolyl group, a 6-benzoxazolyl group, a 7-benzoxazolyl group, a (1,2-benzisoxazol)-3-yl group, a (1,2-benzisoxazol)-4-yl group, a (1,2-benzisoxazol)-5-yl group, a (1,2-benzisoxazol)-6-yl group, a (1,2-benzisoxazol)-7-yl group, a (2,1-benzisoxazol)-3-yl group, a (2,1-benzisoxazol)-4-yl group, a (2,1-benzisoxazol)-5-yl group, a (2,1-benzisoxazol)-6-yl group, a (2,1-benzisoxazol)-7-yl group, a 2-benzothiazolyl group, a 4-benzothiazolyl group, a 5-benzothiazolyl group, a 6-benzothiazolyl group, a 7-benzothiazolyl group, a (1,2-benzisothiazol)-3-yl group, a (1,2-benzisothiazol)-4-yl group, a (1,2-benzisothiazol)-5-yl group, a (1,2-benzisothiazol)-6-yl group, a (1,2-benzisothiazol)-7-yl group, a (2,1-benzisothiazol)-3-yl group, a (2,1-benzisothiazol)-4-yl group, a (2,1-benzisothiazol)-5-yl group, a (2,1-benzisothiazol)-6-yl group, a (2,1-benzisothiazol)-7-yl group, a (1,2,3-benzoxadiazol)-4-yl group, a (1,2,3-benzoxadiazol)-5-yl group, a (1,2,3-benzoxadiazol)-6-yl group, a (1,2,3-benzoxadiazol)-7-yl group, a (2,1,3-benzoxadiazol)-4-yl group, a (2,1,3-benzoxadiazol)-5-yl group, a (1,2,3-benzothiadiazol)-4-yl group, a (1,2,3-benzothiadiazol)-5-yl group, a (1,2,3-benzothiadiazol)-6-yl group, a (1,2,3-benzothiadiazol)-7-yl group, a (2,1,3-benzothiadiazol)-4-yl group, a (2,1,3-benzothiadiazol)-5-yl group, a (1H-benzotriazol)-1-yl group, a (1H-benzotriazol)-4-yl group, a (1H-benzotriazol)-5-yl group, a (1H-benzotriazol)-6-yl group, a (1H-benzotriazol)-7-yl group, a (2H-benzotriazol)-2-yl group, a (2H-benzotriazol)-4-yl group, a (2H-benzotriazol)-5-yl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 3-cinnolinyl group, a 4-cinnolinyl group, a 5-cinnolinyl group, a 6-cinnolinyl group, a 7-cinnolinyl group, a 8-cinnolinyl group, a 2-quinazolinyl group, a 4-quinazolinyl group, a 5-quinazolinyl group, a 6-quinazolinyl group, a 7-quinazolinyl group, a 8-quinazolinyl group, a 2-quinoxalinyl group, a 5-quinoxalinyl group, a 6-quinoxalinyl group, a 1-phthalazinyl group, a 5-phthalazinyl group, a 6-phthalazinyl group, a 2-naphthyridinyl group, a 3-naphthyridinyl group, a 4-naphthyridinyl group, a 2-purinyl group, a 6-purinyl group, a 7-purinyl group, a 8-purinyl group, a 2-pteridinyl group, a 4-pteridinyl group, a 6-pteridinyl group, a 7-pteridinyl group, a 1-carbazolyl group, a 2-carbazolyl group, a 3-carbazolyl group, a 4-carbazolyl group, a 9-carbazolyl group, 2-(α-carbolinyl) group, a 3-(α-carbolinyl) group, a 4-(α-carbolinyl) group, a 5-(α-carbolinyl) group, a 6-(α-carbolinyl) group, a 7-(α-carbolinyl) group, a 8-(α-carbolinyl) group, a 9-(α-carbolinyl) group, a 1-(β-carbolinyl) group, a 3-(β-carbolinyl) group, a 4-(β-carbolinyl) group, a 5-(β-carbolinyl) group, a 6-(β-carbolinyl) group, a 7-(β-carbolinyl) group, a 8-(β-carbolinyl) group, a 9-(β-carbolinyl) group, a 1-(γ-carbolinyl) group, a 2-(γ-carbolinyl) group, a 4-(γ-carbolinyl) group, a 5-(γ-carbolinyl) group, a 6-(γ-carbolinyl) group, a 7-(γ-carbolinyl) group, a 8-(γ-carbolinyl) group, a 9-(γ-carbolinyl) group, a 1-acridinyl group, a 2-acridinyl group, a 3-acridinyl group, a 4-acridinyl group, a 9-acridinyl group, a 1-phenoxazinyl group, a 2-phenoxazinyl group, a 3-phenoxazinyl group, a 4-phenoxazinyl group, a 10-phenoxazinyl group, a 1-phenothiazinyl group, a 2-phenothiazinyl group, a 3-phenothiazinyl group, a 4-phenothiazinyl group, a 10-phenothiazinyl group, a 1-phenazinyl group, a 2-phenazinyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 2-phenanthrolinyl group, a 3-phenanthrolinyl group, a 4-phenanthrolinyl group, a 5-phenanthrolinyl group, a 6-phenanthrolinyl group, a 7-phenanthrolinyl group, a 8-phenanthrolinyl group, a 9-phenanthrolinyl group, a 10-phenanthrolinyl group, a 1-thianthrenyl group, a 2-thianthrenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-phenoxathiinyl group, a 2-phenoxathiinyl group, a 3-phenoxathiinyl group, a 4-phenoxathiinyl group, a thieno[2,3-b]furyl group, a pyrrolo[1,2-b]pyridazinyl group, a pyrazolo[1,5-a]pyridyl group, an imidazo[11,2-a]pyridyl group, an imidazo[1,5-a]pyridyl group, an imidazo[1,2-b]

pyridazinyl group, an imidazo[1,2-a]pyrimidinyl group, a 1,2,4-triazolo[4,3-a]pyridyl group, and 1,2,4-triazolo[4,3-a]pyridazinyl group.

—Alkyl Group—

The alkyl group is, for example, a linear, branched, or cyclic alkyl group, or an alkyl group having a shape of combination thereof. The alkyl group is preferably a $C_1$-$C_{15}$ alkyl group, more preferably a $C_1$-$C_{10}$ alkyl group, particularly preferably a $C_1$-$C_6$ alkyl group.

Examples of the alkyl group include a methyl group, an ethyl group, a n-propyl group, an isopropyl group, a n-butyl group, an isobutyl group, a sec-butyl group, a tert-butyl group, a n-pentyl group, an isopentyl group, a 2-methylbutyl group, a 1-methylbutyl group, a neopentyl group, a 1,2-dimethylpropyl group, a 1-ethylpropyl group, a n-hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a 1-ethylbutyl group, a 1-ethyl-1-methylpropyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a cyclopropyl group, a cyclobutyl group, a cyclopentyl group, a cyclohexyl group, a cycloheptyl group, a cyclooctyl group, a cyclopropylmethyl group, a 1-cyclopropylethyl group, a 2-cyclopropylethyl group, a 3-cyclopropylpropyl, a 4-cyclopropylbutyl group, a 5-cyclopropylpentyl group, a 6-cyclopropylhexyl group, a cyclobutylmethyl group, a cyclopentylmethyl group, a cyclobutylmethyl group, a cyclopentylmethyl group, a cyclohexylmethyl group, a cyclohexylpropyl group, a cyclohexylbutyl group, a cycloheptylmethyl group, a cyclooctylmethyl group, and a 6-cyclooctylhexyl.

Also, the cyclic alkyl group encompasses saturated heterocyclic groups obtained by replacing all of the double bonds in the above heteroaryl groups with single bonds.

—Alkenyl Group—

The alkenyl group is, for example, a linear, branched, or cyclic alkenyl group, or an alkenyl group having a shape of combination thereof. The alkenyl group is preferably a $C_2$-$C_{15}$ alkenyl group, more preferably a $C_2$-$C_{10}$ alkenyl group, particularly preferably a $C_2$-$C_6$ alkenyl group.

The number of double bonds contained in the alkenyl group is not particularly limited, but is, for example, one to several, preferably about 1 or about 2.

Examples of the alkenyl group include a vinyl group, a prop-1-en-1-yl group, an allyl group, an isopropenyl group, a but-1-en-1-yl group, a but-2-en-1-yl group, a but-3-en-1-yl group, a 2-methylprop-2-en-1-yl group, a 1-methylprop-2-en-1-yl group, a penta-1-en-1-yl group, a penta-2-en-1-yl group, a penta-3-en-1-yl group, a pent-4-en-1-yl group, a 3-methylbut-2-en-1-yl group, a 3-methylbut-3-en-1-yl group, a hex-1-en-1-yl group, a hex-2-en-1-yl group, a hex-3-en-1-yl group, a hex-4-en-1-yl group, a hex-5-en-1-yl group, a 4-methylpent-3-en-1-yl group, a 4-methylpent-3-en-1-yl group, a hept-1-en-1-yl group, a hept-6-en-1-yl group, an oct-1-en-1-yl group, an oct-7-en-1-yl group, a nona-1-en-1-yl group, a nona-8-en-1-yl group, a dec-1-en-1-yl group, a dec-9-en-1-yl group, an undec-1-en-1-yl group, an undec-10-en-1-yl group, a dodeca-1-en-1-yl group, a dodeca-11-en-1-yl group, a trideca-1-en-1-yl group, a trideca-12-en-1-yl group, a tetradeca-1-en-1-yl group, a tetradeca-13-en-1-yl group, a pentadeca-1-en-1-yl group, a pentadeca-14-en-1-yl group, a 2-cyclopropen-1-yl group, a 2-cyclobuten-1-yl group, a 2-cyclopenten-1-yl group, a 3-cyclopenten-1-yl group, a 2-cyclohexen-1-yl group, a 1-cyclohexen-1-yl group, a 3-cyclohexen-1-yl group, a 1-cyclobuten-1-yl group, a 1-cyclopenten-1-yl group, a 2-cyclohexen-1-ylmethyl group, and a 2-cyclohexen-1-ylmethyl group.

Also, the cyclic alkenyl group encompasses: partially saturated hydrocarbon ring groups obtained by replacing, with single bond(s), any number of double bond(s) except for at least one double bond in the double bonds of the above aryl groups; partially saturated hetero ring groups obtained by replacing, with single bond(s), any number of double bond(s) except for at least one double bond in the double bonds of the above heteroaryl groups; and the like.

—Alkynyl Group—

The alkynyl group is, for example, a linear alkynyl group or a branched alkynyl group. The alkynyl group is preferably a $C_2$-$C_{15}$ alkynyl group, more preferably a $C_2$-$C_{10}$ alkynyl group, particularly preferably a $C_2$-$C_6$ alkynyl group.

The number of triple bonds contained in the alkynyl group is not particularly limited, but is, for example, one to several, preferably about 1 or about 2. The alkynyl group may contain one to several double bonds. Also, the alkynyl group may be combined with a cyclic alkyl group or a cyclic alkenyl group.

Examples of the alkynyl group include an ethynyl group, a prop-1-yn-1-yl group, a prop-2-yn-1-yl group, a but-1-yn-1-yl group, a but-3-yn-1-yl group, a 1-methylprop-2-yn-1-yl group, a pent-1-yn-1-yl group, a pent-4-yn-1-yl group, a hex-1-yn-1-yl group, a hex-5-yn-1-yl group, a hept-1-yn-1-yl group, a hept-6-yn-1-yl group, an oct-1-yn-1-yl group, an oct-7-yn-1-yl group, a nona-1-yn-1-yl group, a nona-8-yn-1-yl group, a deca-1-yn-1-yl group, a deca-9-yn-1-yl group, an undeca-1-yn-1-yl group, an undeca-10-yn-1-yl group, a dodeca-1-yn-1-yl group, a dodeca-11-yn-1-yl group, a trideca-1-yn-1-yl group, a trideca-12-yn-1-yl group, a tetradeca-1-yn-1-yl group, a tetradeca-13-yn-1-yl group, a pentadeca-1-yn-1-yl group, and a pentadeca-14-yn-1-yl group.

——Substitution——

In the present specification, "substitution" mentioned about organic groups (e.g., the aryl groups, the heteroaryl groups, the alkyl groups, the alkenyl groups, and the alkynyl groups) means that one or two or more substituents are present on the organic groups at chemically possible positions thereon. The kind of the substituent present on the organic groups, the number of the substituents, and the substitution position are not particularly limited. When two or more substituents are present, they may be identical or different.

Examples of the substituent present on the organic groups include halogen atoms, an oxo group, a thioxo group, a nitro group, a nitroso group, a cyano group, an isocyano group, a cyanato group, a thiocyanato group, an isocyanato group, an isothiocyanato group, a hydroxy group, a sulfanyl group, a carboxy group, a sulfanylcarbonyl group, an oxalo group, a mesoxalo group, a thiocarboxy group, a dithiocarboxy group, a carbamoyl group, a thiocarbamoyl group, a sulfo group, a sulfamoyl group, a sulfino group, a sulfinamoyl group, a sulfeno group, a sulfenamoyl group, a phosphono group, a hydroxyl phosphonyl group, $C_1$-$C_6$ alkyl groups, $C_2$-$C_6$ alkenyl groups (e.g., a vinyl group, an allyl group, a 1-propenyl group), $C_2$-$C_6$ alkynyl groups (e.g., an ethynyl group and a 1-propynyl group), $C_1$-$C_6$ alkylidene groups, $C_6$-$C_{10}$ aryl groups, $C_7$-$C_{12}$ aralkyl groups (e.g., a benzyl group, a phenethyl group, a 1-naphthylmethyl group, and a 2-naphthylmethyl group), $C_7$-$C_{12}$ aralkylidene groups (e.g., a benzylidene group, a phenethylidene group, a 1-naphthylmethylidene group, and a 2-naphthylmethylidene group), $C_1$-$C_6$ alkoxy groups, $C_6$-$C_{10}$ aryloxy groups (e.g., a phenoxy group, a 1-naphthyloxy group, and a 2-naphthyloxy group), $C_7$-$C_{12}$ aralkyloxy groups [e.g., a benzyloxy group, a (1-naphthylmethyl)oxy group, and a (2-naphthylmethyl)oxy group], $C_1$-$C_6$ alkylsulfanyl groups (e.g., a methylsulfanyl group and an ethylsulfanyl group), $C_6$-$C_{10}$ arylsulfanyl groups (e.g., a phenylsulfanyl group, a 1-naphthylsulfanyl group, and a 2-naphthylsulfanyl group), $C_7$-$C_{12}$ aralkyloxysulfanyl groups [e.g., a benzylsulfanyl group, a (1-naphthylmethyl)sulfanyl group, and a (2-naphthylmethyl)sulfanyl group], $C_1$-$C_6$ alkanoyl groups (e.g., an acetyl group, a propionyl group, a n-butyryl group, a pivaloyl group), $C_6$-$C_{10}$ aroyl groups (e.g., a benzoyl group, a 1-naphthoyl group, and a 2-naphthoyl group), $C_1$-$C_6$ alkylsulfonyl groups (e.g., a methanesulfonyl group, an ethanesulfonyl group, and a propanesulfonyl group), $C_6$-$C_{10}$ arylsulfonyl groups (e.g., a benzenesulfonyl group, a 1-naphthalenesulfonyl group, and a 2-naphthalenesulfonyl group), $C_1$-$C_6$ alkoxycarbonyl groups, an amino group, a hydrazino group, a hydrazono group, a diazenyl group, an ureido group, a thioureido group, a guanidino group, a carbamoimidoyl group (an amidino group), an azide group, an imino group, a hydroxyamino group, a hydroxyimino group, an aminooxy group, a diazo group, a semicarbazino group, a semicarbazono group, an allophanyl group, a hydantoyl group, a phosphano group, a phosphoroso group, a phopho group, a boryl group, a silyl group, a stannyl group, a selanyl group, oxide groups, heteroaryl groups, and partially saturated or fully saturated heterocyclic groups obtained by replacing some or all of the double bonds in the above heteroaryl groups with single bonds.

These substituents may further be substituted with one kind or two kinds of other substituents. Such examples include $C_1$-$C_6$ halogenated alkyl groups (e.g., a chloromethyl group, a dichloromethyl group, a trichloromethyl group, a difluoromethyl, a trifluoromethyl group, a 2,2,2-trifluoroethyl group, and a pentafluoroethyl group), $C_1$-$C_6$ halogenated alkoxy groups (e.g., a trifluoromethoxy group and a pentafluoroethoxy), carboxy-substituted $C_1$-$C_6$ alkyl groups (e.g., a carboxymethyl group and a carboxyethyl group), and $C_1$-$C_6$ alkyl-substituted amino groups (e.g., a methylamino group and an ethylamino group).

<Copper-Optically Active Phosphine Complex>

The copper-optically active phosphine complex is a complex of copper and an optically active phosphine compound. The optically active phosphine compound is also referred to as an optically active phosphine ligand.

The copper-optically active phosphine complex is obtained from a copper compound and an optically active phosphine compound.

<<Copper Compound>>

The copper compound is not particularly limited and may be appropriately selected depending on the intended purpose, so long as it can form the copper-optically active phosphine complex. Examples of the copper compound include compounds represented by the following General Formula (A).

[Cu(CH$_3$CN)$_4$]X      General Formula (A)

In the General Formula (A), X represents Cl, NO$_3$, ClO$_4$, PF$_6$, or BF$_4$.

Examples of the copper compound include the following compounds, in addition to the compounds represented by the General Formula (A).

[Cu(C$_5$H$_5$N)$_4$]X ("C$_5$H$_5$N" represents pyridine)

[Cu(bpy)$_2$]X ("bpy" represents 2,2'-bipyridine)

[Cu(C$_3$H$_4$N$_2$)$_4$]X$_2$ ("C$_3$H$_4$N$_2$" represents imidazole)

[Cu(phen)$_2$]X$_2$ ("phen" represents 1,10-phenanthroline)

[Cu(C$_{14}$H$_{32}$N$_4$)]X$_2$ ("C$_{14}$H$_{32}$N$_4$" represents 1,4,8,11-tetramethyl-1,4,8,11-tetraazacyclotetradecane)

[CuX(tmpa)]X' ("tmpa" represents tris(2-pyridylmethyl)amine)

[Cu(tmpa)(CH$_3$CN)]X

[{Cu(C$_5$H$_5$N)}$_2$(O$_2$)]X$_2$

[{Cu(tmpa)}$_2$(O$_2$)]X

In the above compounds, X and X' each represent Cl, NO$_3$, ClO$_4$, PF$_6$, or BF$_4$.

<<Optically Active Phosphine Compound>>

The optically active phosphine compound is not particularly limited and may be appropriately selected depending on the intended purpose. Examples of the optically active phosphine compound include cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted phosphorano)benzene (DuPHOS), 1,2-bis(substituted phosphorano)ethane (BPE), 1-((substituted phosphorano)-2-(diphenylphosphino)benzene (UCAP-Ph), 1-(bis(3,5-dimethylphenyl)phosphino)-2-(substituted phosphorano)benzene (UCAP-DM), 1-((substituted phosphorano)-2-(bis(3,5-di(t-butyl)-4-methoxyphenyl)phosphino)benzene (UCAP-DTBM), 1-((substituted phosphorano)-2-(di-naphthalen-1-yl-phosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8',-octahydrobinaphthyl) (H$_8$-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis(diphenylphosphino)-6,6'-dimethyl-1,1'-biphenyl (BICHEP), ((5,6), (5',6')-bis(methylenedioxy)biphenyl-2,2'-diyl) (bisdiphenylphosphine) (SEGPHOS), ((5,6), (5',6')-bis(methylenedioxy)biphenyl-2,2'-diyl) (bis(3,5-dimethylphenyl)phosphine) (DM-SEGPHOS), and ((5,6), (5',6')-bis(methylenedioxy)biphenyl-2,2'-diyl) (bis(3,5-di(tert-butyl)-4-methoxyphenyl)phosphine) (DTBM-SEGPHOS).

From the viewpoints of catalytic activity and stereoselectivity, the optically active phosphine compound is preferably a compound represented by the following General Formula (B), more preferably a compound represented by the following General Formula (B-1) or a compound represented by the following General Formula (B-2).

—General Formula (B), General Formula (B-1), and General Formula (B-2)—

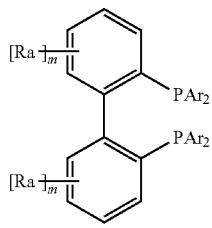

General Formula (B)

In the General Formula (B), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group. m is an integer of 0 to 2. When m is 2, two Ra may be bonded to form a ring structure. Ar represents an aryl group which may have a substituent.

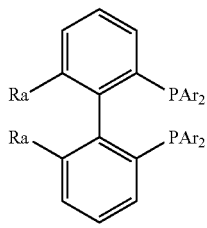

General Formula (B-1)

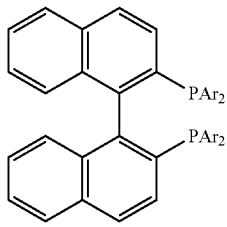

General Formula (B-2)

In the General Formula (B-1), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group. In the General Formula (B-1) and the General Formula (B-2), Ar represents an aryl group which may have a substituent.

Examples of the compound represented by the General Formula (B) include compounds represented by the following General Formula (B-A) and compounds represented by the following General Formula (B-B).

Examples of the General Formula (B-1) include compounds represented by the following General Formula (B-A-1) and compounds represented by the following General Formula (B-B-1).

Examples of the General Formula (B-2) include compounds represented by the following General Formula (B-A-2) and compounds represented by the following General Formula (B-B-2).

—General Formula (B-A), General Formula (B-B), General Formula (B-A-1), General Formula (B-B-1), General Formula (B-A-2), and General Formula (B-B-2)—

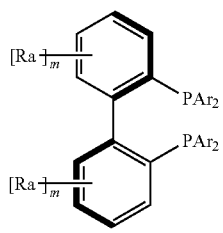

General Formula (B-A)

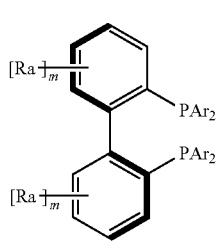

General Formula (B-B)

In the General Formula (B-A) and the General Formula (B-B), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group. m is an integer of 0 to 2. When m is 2, two Ra may be bonded to form a ring structure. Ar represents an aryl group which may have a substituent.

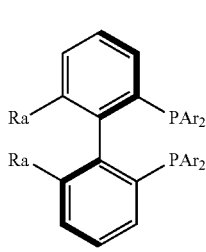

General Formula (B-A-1)

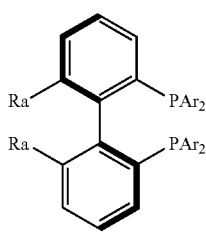

General Formula (B-B-1)

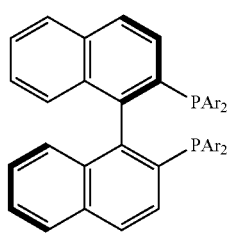

General Formula (B-A-2)

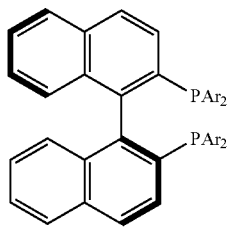

General Formula (B-B-2)

In the General Formula (B-A-1) and the General Formula (B-B-1), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group. In the General Formula (B-A-1), the General Formula (B-B-1), the General Formula (B-A-2), and the General Formula (B-B-2), Ar represents an aryl group which may have a substituent.

——Ra——

Examples of the substituted or unsubstituted aryl group in the Ra include the substituted or unsubstituted aryl groups exemplified in the description of the $R^1$, $R^3$, $R^4$, and $R^{11}$.

Examples of the substituted or unsubstituted heteroaryl group in the Ra include the substituted or unsubstituted heteroaryl groups exemplified in the description of the $R^1$, $R^3$, $R^4$, and $R^{11}$.

Examples of the substituted or unsubstituted alkyl group in the Ra include the substituted or unsubstituted alkyl groups exemplified in the description of the $R^1$, $R^3$, $R^4$, and $R^{11}$.

Examples of the substituted or unsubstituted alkenyl group in the Ra include the substituted or unsubstituted alkenyl groups exemplified in the description of the $R^1$, $R^3$, $R^4$, and $R^{11}$.

Examples of the substituted or unsubstituted alkynyl group in the Ra include substituted or unsubstituted alkynyl groups exemplified in the description of the $R^1$, $R^3$, $R^4$, and $R^{11}$.

Among them, from the viewpoint of stereoselectivity in asymmetric reaction, the Ra is preferably an alkoxy group having 1 to 5 carbon atoms, more preferably an alkoxy group having 1 to 3 carbon atoms, particularly preferably a methoxy group.

——Ar——

The Ar is not particularly limited and may be appropriately selected depending on the intended purpose, so long as it is an aryl group which may have a substituent.

The aryl group is not particularly limited and may be appropriately selected depending on the intended purpose. Examples of the aryl group include the aryl groups exemplified in the description of the Ra. Among them, a phenyl group is preferable.

The substituent in the aryl group which may have a substituent is not particularly limited and may be appropriately selected depending on the intended purpose. Examples of the substituent include alkyl groups, alkoxy groups, and amino groups which may have a substituent.

The alkyl group is preferably an alkyl group having 1 to 10 carbon atoms, more preferably an alkyl group having 1 to 6 carbon atoms, particularly preferably an alkyl group having 1 to 4 carbon atoms. Examples of the alkyl group having 1 to 4 carbon atoms include a methyl group, an ethyl group, a n-propyl group, an isopropyl group, a n-butyl group, an isobutyl group, and a tert-butyl group. Among them, a tert-butyl group is preferable.

The alkoxy group is preferably an alkoxy group having 1 to 10 carbon atoms, more preferably an alkoxy group having 1 to 6 carbon atoms, particularly preferably an alkoxy group having 1 to 4 carbon atoms. Examples of the alkoxy group having 1 to 4 carbon atoms include a methoxy group, an ethoxy group, a n-propyloxy group, an isopropyloxy group, a n-butyloxy group, a sec-butyloxy group, a tert-butyloxy group, and an isobutyloxy group. Among them, a methoxy group is preferable.

Examples of the amino group which may have a substituent include an amino group ($-NH_2$) and dialkylamino groups. Examples of the alkyl group in the dialkylamino groups include alkyl groups having 1 to 3 carbon atoms.

The substitution position of the substituent in the aryl group which may have a substituent is not particularly limited and may be appropriately selected depending on the intended purpose.

The number of the substituents in the aryl group which may have a substituent is not particularly limited and may be appropriately selected depending on the intended purpose. The number of the substituents is, for example, 1 to 3.

<<Method for Synthesizing the Copper-Optically Active Phosphine Complex>>

A method for synthesizing the copper-optically active phosphine complex is not particularly limited and may be appropriately selected depending on the intended purpose. For example, the copper-optically active phosphine complex can be obtained by mixing the copper compound and the optically active phosphine compound in an inert atmosphere, if necessary, in a solvent.

Amounts of the copper compound and the optically active phosphine compound used in the synthesis of the copper-optically active phosphine complex are not particularly limited and may be appropriately selected depending on the intended purpose. The optically active phosphine compound is preferably 1.0 mol to 2.0 mol, more preferably 1.0 mol to 1.3 mol, relative to 1.0 mol of the copper compound. When the amount of the optically active phosphine compound relative to 1.0 mol of the copper compound is less than 1.0 mol, stereoselectivity may decrease. When it is more than 2.0 mol, catalytic activity may decrease. The amount falling within the more preferable range is advantageous from the viewpoints of stereoselectivity and catalytic activity.

The inert atmosphere is not particularly limited and may be appropriately selected depending on the intended purpose. Examples of the inert atmosphere include an argon atmosphere.

The solvent is not particularly limited and may be appropriately selected depending on the intended purpose. Examples of the solvent include THF (tetrahydrofuran) and toluene. The toluene is preferably anhydrous toluene.

A reaction temperature in the synthesis of the copper-optically active phosphine complex is not particularly limited and may be appropriately selected depending on the intended purpose. The reaction temperature is, for example, room temperature. The room temperature is, for example, 20° C. to 300° C.

A reaction time in the synthesis of the copper-optically active phosphine complex is not particularly limited and may be appropriately selected depending on the intended purpose. The reaction time is, for example, 0.5 hours to 2 hours.

<Reaction Conditions for Method for Producing the Optically Active α-Trifluoromethyl-β-Amino Acid Derivative>

The method for producing the optically active α-trifluoromethyl-β-amino acid derivative uses the copper-optically active phosphine complex and, if necessary, a base.

<<Amount of Copper-Optically Active Phosphine Complex>>

An amount of the copper-optically active phosphine complex used in the reaction between the compound represented by the General Formula (1) and the compound represented by the General Formula (2) is not particularly limited and may be appropriately selected depending on the intended purpose. The amount of the copper-optically active phosphine complex is preferably 1 mol % to 20 mol %, more preferably 3 mol % to 15 mol %, relative to the compound represented by the General Formula (2). When the amount of the copper-optically active phosphine complex is less than 1 mol %, stereoselectivity may decrease. When it is more than 20 mol %, the catalytic amount is large, which may lead to increase in synthesis cost. The amount of the copper-optically active phosphine complex falling with the more preferable range is advantageous in that high stereoselectivity is achieved and asymmetric Mannich reaction can be performed inexpensively.

<<Amount of the Compound Represented by General Formula (1)>>

An amount of the compound represented by the General Formula (1) used in the reaction between the compound represented by the General Formula (1) and the compound represented by the General Formula (2) is not particularly limited and may be appropriately selected depending on the intended purpose. The amount of the compound represented by the General Formula (1) is preferably 1 mol or more, more preferably 1 mol to 3 mol, relative to 1 mol of the compound represented by the General Formula (2). When the amount of the compound represented by the General Formula (1) is less than 1 mol relative to 1 mol of the compound represented by the General Formula (2), reaction yield may decrease. When it is more than 3 mol, purification may take efforts. The amount of the compound represented by the General Formula (1) within the more preferable range is advantageous in that the reaction yield is good and the synthesis is possible without taking efforts for, for example, purification.

<<Base>>

The base is not particularly limited and may be appropriately selected depending on the intended purpose. Examples of the base include guanidine bases, amidine bases, phosphazene bases, and lithium compounds represented by the following General Formula (I).

$$\text{LiOR}^{201} \quad\quad \text{General Formula (I)}$$

In the General Formula (I), $R^{201}$ represents a substituted or unsubstituted aryl group or a substituted or unsubstituted alkyl group.

—Guanidine Base—

The guanidine base is not particularly limited and may be appropriately selected depending on the intended purpose, so long as it is a base having a guanidine skeleton. Examples of the guanidine base include guanidine compounds represented by the following General Formula (C).

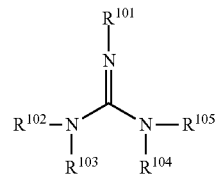

General Formula (C)

In the General Formula (C), $R^{101}$ to $R^{105}$ each independently represent a hydrogen atom or an alkyl group having 1 to 6 carbon atoms. $R^{101}$ and $R^{102}$ may form a ring structure with N binding to the $R^{101}$, N binding to the $R^{102}$, and C binding to these two N. $R^{103}$ and $R^{104}$ may form a ring structure with N binding to the $R^{103}$, N binding to the $R^{104}$, and C binding to these two N.

Examples of the guanidine compound include guanidine compounds expressed by the following structural formulas.

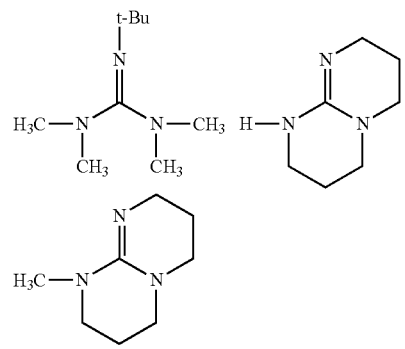

Here, "t-Bu" represents a tert-butyl group.

—Amidine Base—

The amidine base is not particularly limited and may be appropriately selected depending on the intended purpose, so long as it is a base having an amidine skeleton. Examples of the amidine base include 1,8-diazabicyclo[5.4.0]undec-7-ene (DBU) and 1,5-diazabicyclo[4.3.0]non-5-ene (DBN).

—Phosphazene Base—

The phosphazene base is not particularly limited and may be appropriately selected depending on the intended purpose, so long as it is a base having a phosphazene skeleton. Examples of the phosphazene base include alkylimino-tris(dimethylamino)phosphorane (with the proviso that the alkyl is an alkyl group having 1 to 8 carbon atoms) and alkylimino-tris(pyrrolidino)phosphorane (with the proviso that the alkyl is an alkyl group having 1 to 8 carbon atoms).

—Lithium Compound Represented by General Formula (I)—

Examples of the lithium compound represented by the General Formula (I) include methoxylithium, ethoxylithium, n-propoxylithium, i-propoxylithium, n-butoxylithium, sec-butoxylithium, t-butoxylithium, pentyloxylithium, hexyloxylithium, hetyloxylithium, octyloxylithium, phenoxylithium, 4-methylphenoxylithium, 4-methoxyphenoxylithium, 2,6-di-tert-butyl-4-methylphenoxylithium, and benzyloxylithium.

—Amount of Base—

An amount of the base used in the reaction between the compound represented by the General Formula (1) and the compound represented by the General Formula (2) is not particularly limited and may be appropriately selected depending on the intended purpose. From the viewpoints of catalytic activity and stereoselectivity, the amount of the base is preferably 1 mol % to 20 mol %, more preferably 3 mol % to 15 mol %, relative to the compound represented by the General Formula (2).

<<Organic Solvent>>

An organic solvent is preferably used in the reaction between the compound represented by the General Formula (1) and the compound represented by the General Formula (2). The organic solvent is not particularly limited and may be appropriately selected depending on the intended purpose. Examples of the organic solvent include toluene, tetrahydrofuran (THF), and methylene chloride. An amount of the organic solvent used is not particularly limited and may be appropriately selected depending on the intended purpose.

<<Reaction Temperature>>

A reaction temperature in the reaction between the compound represented by the General Formula (1) and the compound represented by the General Formula (2) is not particularly limited and may be appropriately selected depending on the intended purpose. The reaction temperature is preferably 10° C. to 40° C., more preferably room temperature. The room temperature is a temperature of 20° C. to 30° C.

<<Reaction Time>>

A reaction time in the reaction between the compound represented by the General Formula (1) and the compound represented by the General Formula (2) is not particularly limited and may be appropriately selected depending on the intended purpose. The reaction time is preferably 1 hour to 72 hours, more preferably 6 hours to 36 hours, particularly preferably 10 hours to 28 hours. When the reaction time is less than 1 hour, reaction yield may decrease. When the reaction time is more than 72 hours, side reaction may proceed. The reaction time falling within the above particularly preferable range is advantageous in terms of reaction yield.

EXAMPLES

The present invention will next be described in detail by way of Examples. The present invention, however, should not be construed as being limited to the Examples.

Note that, in the following Examples, "THF" denotes "tetrahydrofuran". "Me" denotes "methyl group". "iPr" denotes "isopropyl group". "Ph" denotes "phenyl group". "Boc" denotes "tert-butoxycarbonyl group". "t-Bu" denotes "tert-butyl group". "C₆H₄" denotes "phenylene group".

Example 1

<Synthesis of Optically Active α-Trifluoromethyl-β-Amino Acid Derivative>

In accordance with the following reaction scheme, synthesis of an optically active α-trifluoromethyl-β-amino acid derivative (the following Compound 3aa) was performed.

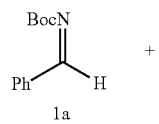

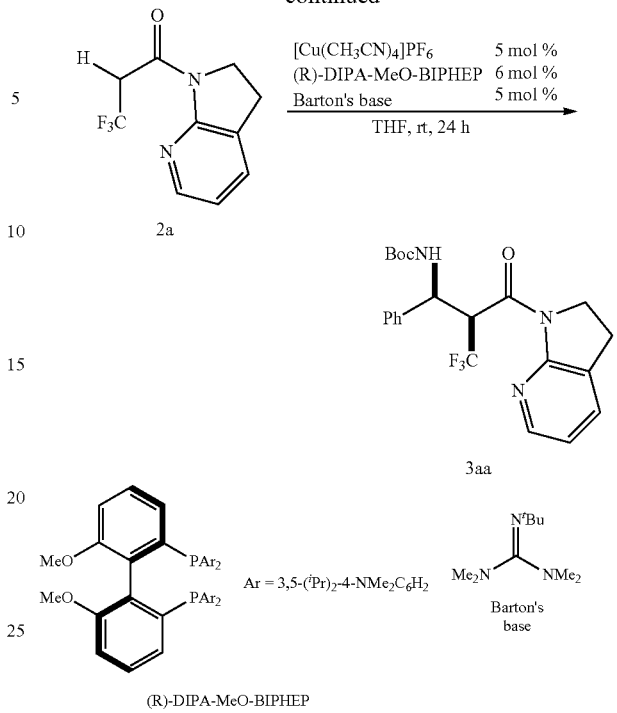

A 20 mL evacuation test tube was dried in vacuum with heating. [Cu(CH₃CN)₄]PF₆ (11.1 mg, 0.03 mmol, product of sigma-aldrich Co.) and (R)-DIPA-MeO-BIPHEP (39.3 mg, 0.036 mmol, product of sigma-aldrich Co.) were weighed and placed in the test tube. THF (0.9 mL) was added to the test tube at room temperature, followed by stirring for 1 hour under Ar, to thereby prepare a copper catalyst solution (0.033 M/THF).

Another 20 mL evacuation test tube was dried in vacuum with heating. α-CF₃ amide 2a (23.0 mg, 0.1 mmol, synthesized by usual amide condensation) was to weighed and placed in the test tube. Under an Ar atmosphere, the copper catalyst solution (0.15 mL, 0.005 mmol) and a Barton base (2% v/v in THF, 0.05 mL, product of sigma-aldrich Co.) were added to the test tube at room temperature, followed by stirring for 5 minutes. Boc imine 1a [41.9 μL, 0.2 mmol, synthesized with reference to documents [(a) A. M. Kanazawa, J. Denis, A. E. Greene, J. Org. Chem. 1994, 59, 1238, and (b) B. E. Love, P. S. Raje, T. C. Williams, Synlett 1994, 493.]] was added thereto, followed by stirring for 24 hours at room temperature.

The reaction solution was purified by preparative thin-layer chromatography (hexane/ethyl acetate=2/1 (v/v)), to thereby obtain product 3aa (40.8 mg, 94%).

The optical purity was determined by HPLC (98% ee; Chiralpak IA (φ0.46 cm×25 cm) isopropanol/hexane=1/9 (v/v), flow rate 1.0 mL/min, detection 254 nm, retention time 12.0 minutes (syn-minor), 13.7 minutes (syn-major), syn/anti>20/1).

Examples 2 to 7

Optically active α-trifluoromethyl-β-amino acid derivatives were synthesized in the same manner as in Example 1 except that the Boc imine, the catalytic amount of the copper, and the amount of the base were changed as presented in the following scheme and Table 1. The yield, syn/anti ratio (dr), and optical purity (ee) are presented in Table 1.

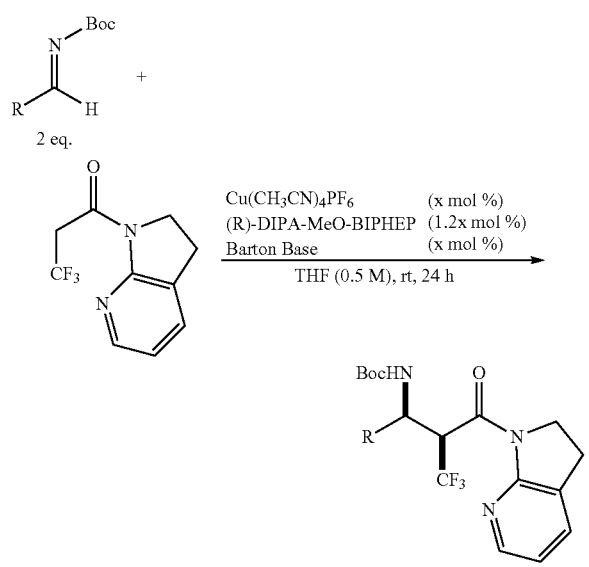

TABLE 1

| Examples | R | x | yield (%)[a] | dr[b] | ee (%)[c] |
|---|---|---|---|---|---|
| 1 | C$_6$H$_5$ | 5 | 94 | >20/1 | 98 |
| 2 | 4-MeO—C$_6$H$_4$ | 5 | 95 | >20/1 | 98 |
| 3 | 4-F—C$_6$H$_4$ | 10 | 92 | >20/1 | 99 |
| 4 | 3-vinyl-C$_6$H$_4$ | 10 | 92 | >20/1 | 96 |
| 5 | 3-MeO—C$_6$H$_4$ | 10 | 90 | >20/1 | 96 |
| 6 | 2-thienyl | 10 | 91 | >20/1 | 94 |
| 7 | 4-Cl—C$_6$H$_4$ | 10 | 91 | >20/1 | 99 |

[a] isolation yield
[b, c] determined by chiral HPLC

The Boc imine used in Examples 2 to 7 was synthesized with reference to documents [(a) A. M. Kanazawa, J. Denis, A. E. Greene, J. Org. Chem. 1994, 59, 1238, and (b) B. E. Love, P. S. Raje, T. C. Williams, Synlett 1994, 493.].

Example 8

<Synthesis of Optically Active α-Trifluoromethyl-β-Amino Acid Derivative>

In accordance with the following reaction scheme, synthesis of an optically active α-trifluoromethyl-β-amino acid derivative (the following Compound 3ab) was performed.

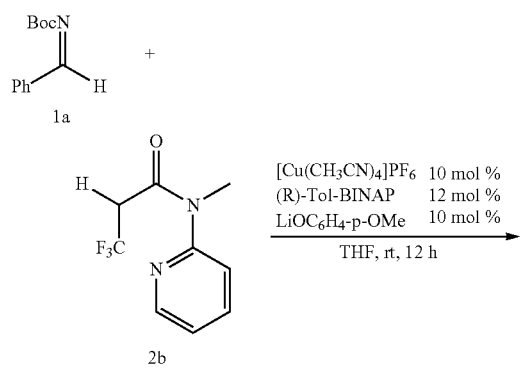

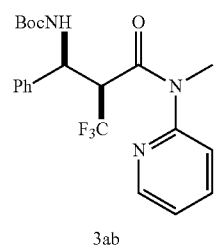

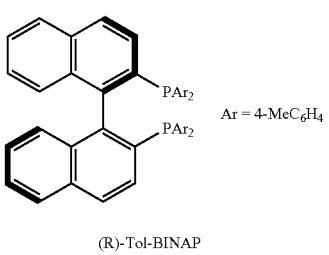

A 20 mL evacuation test tube was dried in vacuum with heating. [Cu(CH$_3$CN)$_4$]PF$_6$ (3.7 mg, 0.01 mmol, product of sigma-aldrich Co.) and (R)-Tol-BINAP (8.2 mg, 0.012 mmol, product of sigma-aldrich Co.) were weighed and placed in the test tube. THF (0.4 mL) was added to the test tube at room temperature, followed by stirring for 1 hour under Ar. α-CF$_3$ amide 2b (21.8 mg, 0.1 mmol, synthesized by usual amide condensation) and LiO—C$_6$H$_4$-p-OMe [0.1 mL, 0.01 mmol, synthesized by mixing 0.1 M/THF, n-BuLi (product of KANTO CHEMICAL Co.) and HO—C$_6$H$_4$-p-OMe (product of Wako Pure Chemical Industries, Ltd.) in equimolar amounts] were sequentially added thereto, followed by stirring for 5 minutes. The Boc imine 1a [41.9 µL, 0.2 mmol, synthesized with reference to documents [(a) A. M. Kanazawa, J. Denis, A. E. Greene, J. Org. Chem. 1994, 59, 1238, and (b) B. E. Love, P. S. Raje, T. C. Williams, Synlett 1994, 493.]] was added thereto, followed by stirring for 12 hours at room temperature.

The reaction solution was concentrated and the obtained crude product was tested for diastereoselectivity by $^1$H NMR measurement (syn/anti=2/1). The crude product was purified by preparative thin-layer chromatography (hexane/ethyl acetate=2/1 (v/v)), to thereby obtain product 3ab (26.6 mg, 63%).

The optical purity was determined by HPLC (84% ee; Chiralpak IA (φ0.46 cm×25 cm) isopropanol/hexane=1/40 (v/v), flow rate 1.0 mL/min, detection 254 nm, retention time 34.7 minutes (minor), 40.6 minutes (major)).

The structure and the $^1$H NMR measurement results of the obtained optically active α-trifluoromethyl-β-amino acid derivative are presented below.

Example 1 and Example 8

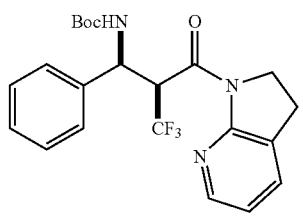 [SMILES: CC(C)(C)OC(=O)N[C@H](c1ccccc1)[C@@H](C(=O)N1CCc2cccnc21)C(F)(F)F]

¹H NMR (600 MHz, CDCl₃): δ8.18 (brs, 1H), 7.45 (d, J=6.8 Hz, 1H), 7.35 (d, J=6.5 Hz, 2H), 7.20-7.16 (m, 3H), 6.95-6.92 (m, 1H), 6.19 (t, J=7.8 Hz, 1H), 5.57-5.54 (m, 1H), 5.46 (d, J=8.9 Hz, 1H), 4.06-4.01 (m, 1H), 3.79-3.74 (m, 1H), 2.98-2.92 (m, 1H), 2.88-2.83 (m, 1H), 1.39 (s, 9H).

Example 2

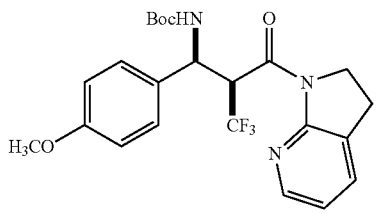 [SMILES: COc1ccc([C@@H](NC(=O)OC(C)(C)C)[C@@H](C(=O)N2CCc3cccnc32)C(F)(F)F)cc1]

1H NMR (400 MHz, CDCl₃): δ8.16 (d, J=4.4 Hz, 1H), 7.44 (d, J=7.1 Hz, 1H), 7.23 (brs, 2H), 6.93 (t, J=5.3 Hz, 1H), 6.70 (brs, 2H), 6.19 (brs, 1H), 5.48 (brs, 1H), 5.38 (brs, 1H), 4.01 (brs, 1H), 3.76 (brs, 1H), 3.71 (s, 3H), 2.92 (brs, 2H), 1.38 (s, 9H).

Example 3

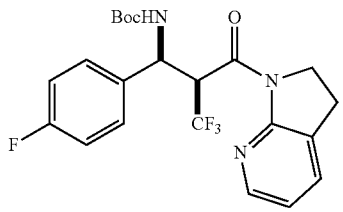 [SMILES: CC(C)(C)OC(=O)N[C@H](c1ccc(F)cc1)[C@@H](C(=O)N1CCc2cccnc21)C(F)(F)F]

¹H NMR (400 MHz, CDCl₃): δ8.16 (d, J=4.8 Hz, 1H), 7.47 (d, J=7.1 Hz, 1H), 7.33 (brs, 2H), 6.97-6.89 (m, 3H), 6.19 (brs, 1H), 5.51 (brs, 1H), 5.46 (brs, 1H), 4.04 (brs, 1H), 3.77 (brs, 1H), 2.98-2.93 (m, 2H), 1.38 (s, 9H).

Example 4

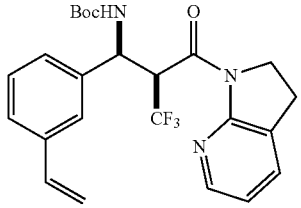 [SMILES: C=Cc1cccc([C@@H](NC(=O)OC(C)(C)C)[C@@H](C(=O)N2CCc3cccnc32)C(F)(F)F)c1]

¹H NMR (400 MHz, CDCl₂): δ8.17 (d, J=4.8 Hz, 1H), 7.44-7.37 (m, 2H), 7.22-7.13 (m, 3H), 6.94-6.91 (m, 1H), 6.58-6.51 (m, 1H), 6.23 (brs, 1H), 5.60-5.42 (m, 3H), 5.14 (d, J=10.8 Hz, 1H), 3.99 (brs, 1H), 3.73 (brs, 1H), 2.90-2.84 (m, 2H), 1.39 (s, 9H).

Example 5

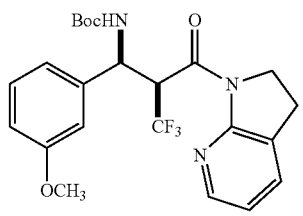 [SMILES: COc1cccc([C@@H](NC(=O)OC(C)(C)C)[C@@H](C(=O)N2CCc3cccnc32)C(F)(F)F)c1]

¹H NMR (400 MHz, CDCl₃): δ8.18 (d, J=4.6 Hz, 1H), 7.46 (d, J=7.3 Hz, 1H), 7.12 (brs, 1H), 6.95-6.92 (m, 3H), 6.71 (d, J=7.6 Hz, 1H), 6.19 (brs, 1H), 5.53 (brs, 1H), 5.42 (brs, 1H), 4.04 (brs, 1H), 3.79 (brs, 1H), 3.68 (s, 3H), 2.95 (brs, 2H), 1.39 (s, 9H).

Example 6

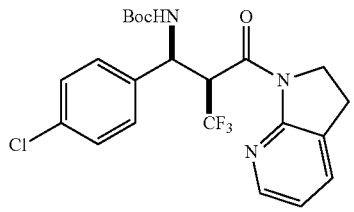 [SMILES: CC(C)(C)OC(=O)N[C@H](c1ccc(Cl)cc1)[C@@H](C(=O)N1CCc2cccnc21)C(F)(F)F]

¹H NMR (600 MHz, CDCl₃): δ8.16 (d, J=4.1 Hz, 1H), 7.49 (d, J=7.6 Hz, 1H), 7.32 (d, J=7.6 Hz, 2H), 7.19 (d, J=7.6 Hz, 2H), 6.97-6.95 (m, 1H), 6.16 (t, J=7.2 Hz, 1H), 5.52-5.47 (m, 2H), 4.08-4.06 (m, 1H), 3.83-3.78 (m, 1H), 3.02-2.89 (m, 2H), 1.38 (s, 9H).

Example 7

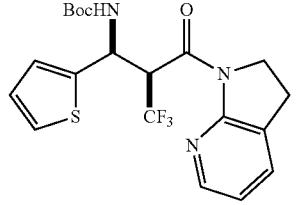 [SMILES: CC(C)(C)OC(=O)N[C@H](c1cccs1)[C@@H](C(=O)N1CCc2cccnc21)C(F)(F)F]

¹H NMR (600 MHz, CDCl₃): δ8.18 (d, J=4.5 Hz, 1H), 7.48 (d, J=6.8 Hz, 1H), 7.13 (d, J=4.4 Hz, 1H), 7.01 (brs, 1H), 6.95-6.93 (m, 1H), 6.85 (brs, 1H), 6.20 (t, J=7.6 Hz, 1H), 5.86-5.83 (m, 1H), 5.37 (d, J=9.7 Hz, 1H), 4.13-4.07 (m, 1H), 3.89-3.84 (m, 1H), 3.02-2.96 (m, 2H), 1.40 (s, 9H).

INDUSTRIAL APPLICABILITY

The method of the present invention for producing an optically active α-trifluoromethyl-β-amino acid derivative is able to synthesize the optically active α-trifluoromethyl-β-amino acid derivative at high yield and catalytically without necessitating activating reagents more than equivalent amounts. Thus, the method of the present invention can be suitably used as a method for producing an optically active α-trifluoromethyl-β-amino acid derivative.

Aspects of the present invention are, for example, as follows.

<1> A method for producing an optically active α-trifluoromethyl-β-amino acid derivative, the method including:

allowing a compound represented by the following General Formula (1) and a compound represented by the following General Formula (2) to react in the presence of a copper-optically active phosphine complex obtained from a copper compound and an optically active phosphine compound, to thereby obtain an optically active α-trifluoromethyl-β-amino acid derivative represented by the following General Formula (3):

General Formula (1)

General Formula (2)

General Formula (3)

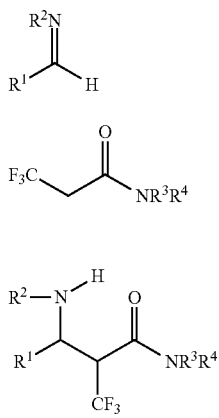

where in the General Formulas (1) to (3), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, $R^3$ and $R^4$ each independently represent a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and $R^3$ and $R^4$ may form a ring structure with N.

<2> The method for producing an optically active α-trifluoromethyl-β-amino acid derivative according to <1>, wherein the $R^2$ in the General Formula (1) and the General Formula (3) is a tert-butoxycarbonyl group.

<3> The method for producing an optically active α-trifluoromethyl-β-amino acid derivative according to <1> or <2>, wherein the $R^1$ in the General Formula (1) and the General Formula (3) is a substituted or unsubstituted aryl group.

<4> The method for producing an optically active α-trifluoromethyl-β-amino acid derivative according to any one of <1> to <3>, wherein the compound represented by the General Formula (2) is a compound represented by the following General Formula (2-1), and the optically active α-trifluoromethyl-β-amino acid derivative represented by the General Formula (3) is an optically active α-trifluoromethyl-β-amino acid derivative represented by the following General Formula (3-1):

General Formula (2-1)

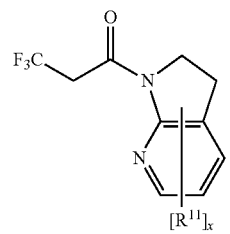

General Formula (3-1)

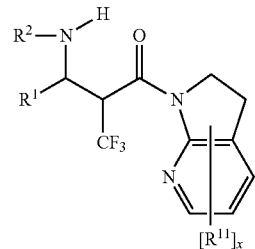

where in the General Formula (2-1) and the General Formula (3-1), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, $R^{11}$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and x is an integer of 0 to 7 (where when x is 2 or more, $R^{11}$ may be identical or different).

<5> The method for producing an optically active α-trifluoromethyl-β-amino acid derivative according to any one of <1> to <4>, wherein the copper compound is a compound represented by the following General Formula (A):

$[Cu(CH_3CN)_4]X$             General Formula (A)

where in the General Formula (A), X represents Cl, $NO_3$, $ClO_4$, $PF_6$, or $BF_4$.

<6> The method for producing an optically active α-trifluoromethyl-β-amino acid derivative according to any one of <1> to <5>, wherein the optically active phosphine compound is a compound represented by the following General Formula (B):

General Formula (B)

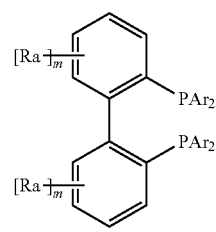

where in the General Formula (B), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, m is an integer of 0 to 2, when m is 2, two Ra may be bonded to form a ring structure, and Ar represents an aryl group which may have a substituent.

<7> The method for producing an optically active α-trifluoromethyl-β-amino acid derivative according to any one of <1> to <6>, wherein the optically active phosphine compound is a compound represented by the following General Formula (B-1) or a compound represented by the following General Formula (B-2):

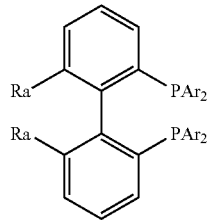

General Formula (B-1)

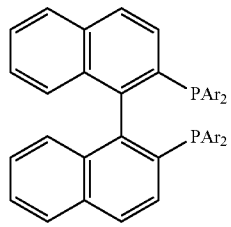

General Formula (B-2)

where in the General Formula (B-1), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and in the General Formula (B-1) and the General Formula (B-2), Ar represents an aryl group which may have a substituent.

The invention claimed is:

1. A method for producing an optically active α-trifluoromethyl-β-amino acid derivative, the method comprising:
allowing a compound represented by the following General Formula (1) and a compound represented by the following General Formula (2) to react in the presence of a copper-optically active phosphine complex obtained from a copper compound and an optically active phosphine compound, to thereby obtain an optically active α-trifluoromethyl-β-amino acid derivative represented by the following General Formula (3):

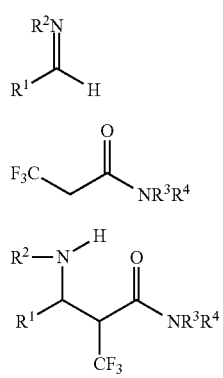

General Formula (1)

General Formula (2)

General Formula (3)

where in the General Formulas (1) to (3), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, $R^3$ and $R^4$ each independently represent a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and $R^3$ and $R^4$ may form a ring structure with N.

2. The method for producing an optically active α-trifluoromethyl-β-amino acid derivative according to claim 1, wherein the $R^2$ in the General Formula (1) and the General Formula (3) is a tert-butoxycarbonyl group.

3. The method for producing an optically active α-trifluoromethyl-β-amino acid derivative according to claim 1, wherein the $R^1$ in the General Formula (1) and the General Formula (3) is a substituted or unsubstituted aryl group.

4. The method for producing an optically active α-trifluoromethyl-β-amino acid derivative according to claim 1, wherein the compound represented by the General Formula (2) is a compound represented by the following General Formula (2-1), and the optically active α-trifluoromethyl-β-amino acid derivative represented by the General Formula (3) is an optically active α-trifluoromethyl-β-amino acid derivative represented by the following General Formula (3-1):

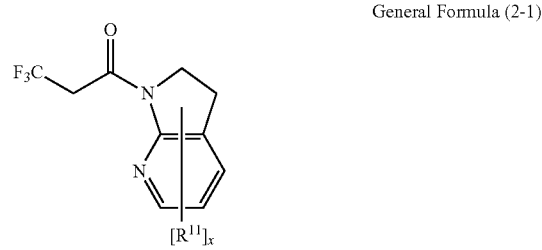

General Formula (2-1)

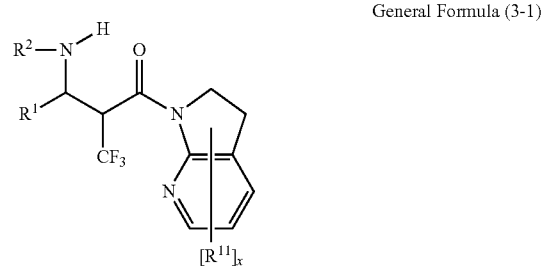

General Formula (3-1)

where in the General Formula (2-1) and the General Formula (3-1), $R^1$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, $R^2$ represents a protective group of N, $R^{11}$ represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and x is an integer of 0 to 7 (where when x is 2 or more, $R^{11}$ may be identical or different).

5. The method for producing an optically active α-trifluoromethyl-β-amino acid derivative according to claim 1, wherein the copper compound is a compound represented by the following General Formula (A):

[Cu(CH₃CN)₄]X    General Formula (A)

where in the General Formula (A), X represents Cl, NO₃, ClO₄, PF₆, or BF₄.

6. The method for producing an optically active α-trifluoromethyl-β-amino acid derivative according to claim 1, wherein the optically active phosphine compound is a compound represented by the following General Formula (B):

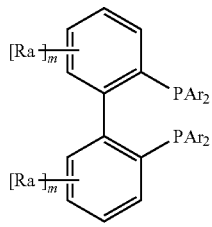

General Formula (B)

where in the General Formula (B), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, m is an integer of 0 to 2, when m is 2, two Ra may be bonded to form a ring structure, and Ar represents an aryl group which may have a substituent.

7. The method for producing an optically active α-trifluoromethyl-β-amino acid derivative according to claim 1, wherein the optically active phosphine compound is a compound represented by the following General Formula (B-1) or a compound represented by the following General Formula (B-2):

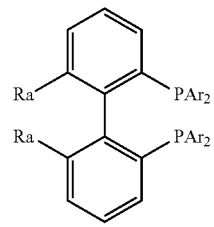

General Formula (B-1)

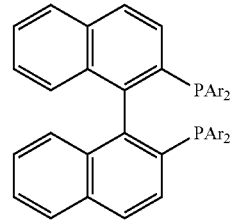

General Formula (B-2)

where in the General Formula (B-1), Ra each independently represents a substituted or unsubstituted aryl group, a substituted or unsubstituted heteroaryl group, a substituted or unsubstituted alkyl group, a substituted or unsubstituted alkenyl group, or a substituted or unsubstituted alkynyl group, and in the General Formula (B-1) and the General Formula (B-2), Ar represents an aryl group which may have a substituent.

* * * * *